(12) United States Patent
Ackermann et al.

(10) Patent No.: US 8,889,899 B2
(45) Date of Patent: Nov. 18, 2014

(54) TRANSESTERIFICATION METHODS

(75) Inventors: Jochen Ackermann, Muehltal (DE); Alexander May, Darmstadt (DE); Udo Gropp, Bad Endorf (DE); Hermann Siegert, Seeheim-Jugenheim (DE); Bernd Vogel, Wiesbaden (DE); Soenke Broecker, Ober-Ramstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 11/914,493

(22) PCT Filed: May 12, 2006

(86) PCT No.: PCT/EP2006/062283
§ 371 (c)(1),
(2), (4) Date: Nov. 20, 2007

(87) PCT Pub. No.: WO2006/122912
PCT Pub. Date: Nov. 23, 2006

(65) Prior Publication Data
US 2008/0194862 A1    Aug. 14, 2008

(30) Foreign Application Priority Data

May 20, 2005 (DE) .......................... 10 2005 023 976

(51) Int. Cl.
| C07C 67/02 | (2006.01) |
| C07C 67/03 | (2006.01) |
| C07C 67/10 | (2006.01) |
| B01D 3/14  | (2006.01) |

(52) U.S. Cl.
CPC .. B01D 3/14 (2013.01); C07C 67/10 (2013.01)
USPC ......................................................... 560/217

(58) Field of Classification Search
None
See application file for complete search history.

(56) References Cited

U.S. PATENT DOCUMENTS

| 3,836,576 A | 9/1974 | Falize et al. |
| 4,458,088 A * | 7/1984 | Hardman et al. ............... 560/96 |
| 6,444,842 B1 | 9/2002 | Gerberich et al. |
| 6,743,407 B2 | 6/2004 | Schaefer et al. |
| 6,977,310 B2 | 12/2005 | Ackermann et al. |
| 6,979,432 B2 | 12/2005 | Schaefer et al. |
| 7,288,402 B2 | 10/2007 | Osswald et al. |
| 7,429,370 B2 | 9/2008 | Von Hippel et al. |

(Continued)

FOREIGN PATENT DOCUMENTS

| EP | 0 193 799 | 9/1986 |
| EP | 0 506 070 | 9/1992 |

(Continued)

OTHER PUBLICATIONS

U.S. Appl. No. 11/915,042, filed Nov. 20, 2007, Ackermann, et al.

(Continued)

*Primary Examiner* — Clinton Brooks
(74) *Attorney, Agent, or Firm* — Oblon, Spivak, McClelland, Maier & Neustadt, L.L.P.

(57) ABSTRACT

The present invention relates to processes for transesterification, comprising the steps of
  A) mixing an organic acid a) with an ester b) and
  B) transferring the alcohol radical of the ester b) to the acid a) to obtain the ester of the acid a) and the acid of the ester b),
step B) being carried out in a still.

12 Claims, 1 Drawing Sheet

(56) References Cited

U.S. PATENT DOCUMENTS

| | | |
|---|---|---|
| 7,491,521 B2 | 2/2009 | Osswald et al. |
| 8,461,375 B2 * | 6/2013 | Ackerman et al. ............ 560/217 |
| 2004/0242924 A1 | 12/2004 | Zehner et al. |
| 2006/0211880 A1 | 9/2006 | Ackerman et al. |
| 2007/0149811 A1 | 6/2007 | Schleep et al. |
| 2007/0173664 A1 | 7/2007 | Krill et al. |
| 2008/0194875 A1 * | 8/2008 | Ackermann et al. .......... 562/599 |
| 2008/0248538 A1 | 10/2008 | Osswald et al. |
| 2009/0118533 A1 | 5/2009 | Broell et al. |
| 2009/0149674 A1 | 6/2009 | Schleep et al. |

FOREIGN PATENT DOCUMENTS

| | | | |
|---|---|---|---|
| EP | 0 765 859 | | 4/1997 |
| EP | 0 916 643 | | 5/1999 |
| EP | 0 983 993 | | 3/2000 |
| EP | 1 186 592 | | 3/2002 |
| GB | 341 730 | | 1/1931 |
| GB | 341730 A | * | 1/1931 |
| GB | 1 143 943 | | 2/1969 |
| JP | 2003-160533 | | 6/2003 |
| KR | 1995-0000643 | | 1/1995 |
| KR | 1020040019389 | | 3/2004 |
| WO | WO2004063140 | * | 7/2004 .............. C07C 67/03 |

OTHER PUBLICATIONS

U.S. Appl. No. 11/995,206, filed Jan. 10, 2008, Sarcinelli, et al.
U.S. Appl. No. 60/893,788, filed Mar. 8, 2007, May, et al.
U.S. Appl. No. 12/517,199, filed Jun. 2, 2009, Gropp, et al.
U.S. Appl. No. 12/422,123, filed Mar. 20, 2009, Gropp, et al.
U.S. Appl. No. 12/516,629, filed May 28, 2009, Gropp, et al.
U.S. Appl. No. 12/517,366, filed Jun. 3, 2009, Gropp, et al.
U.S. Appl. No. 12/515,545, filed May 20, 2009, Gropp, et al.
U.S. Appl. No. 12/515,964, filed May 22, 2009, Gropp, et al.
U.S. Appl. No. 12/517,673, filed Jun. 4, 2009, Gropp, et al.
U.S. Appl. No. 12/298,034, filed Oct. 22, 2008, May, et al.
U.S. Appl. No. 12/300,189, filed Nov. 10, 2008, Broell, et al.
U.S. Appl. No. 12/299,217, filed Oct. 31, 2008, Broell, et al.
U.S. Appl. No. 12/307,773, filed Jan. 7, 2009, Ackermann, et al.
U.S. Appl. No. 12/441,145, filed Mar. 13, 2009, May, et al.
U.S. Appl. No. 12/515,036, filed May 15, 2009, May, et al.
U.S. Appl. No. 12/443,784, filed Mar. 31, 2009, Vogel, et al.
U.S. Appl. No. 12/442,415, filed Mar. 23, 2009, Vogel, et al.
U.S. Appl. No. 12/303,161, filed Dec. 2, 2008, Marx, et al.
Office Action issued Jul. 10, 2013 in Canadian Patent Application No. 2,608,317.
Office Action issued Mar. 25, 2013, in Korean Office Action Patent Application No. 10-2007-7026895 w/ English translation.
English translation of Office Action mailed Mar. 29, 2011 in corresponding Japanese Patent Application No. 2008-511683.

* cited by examiner

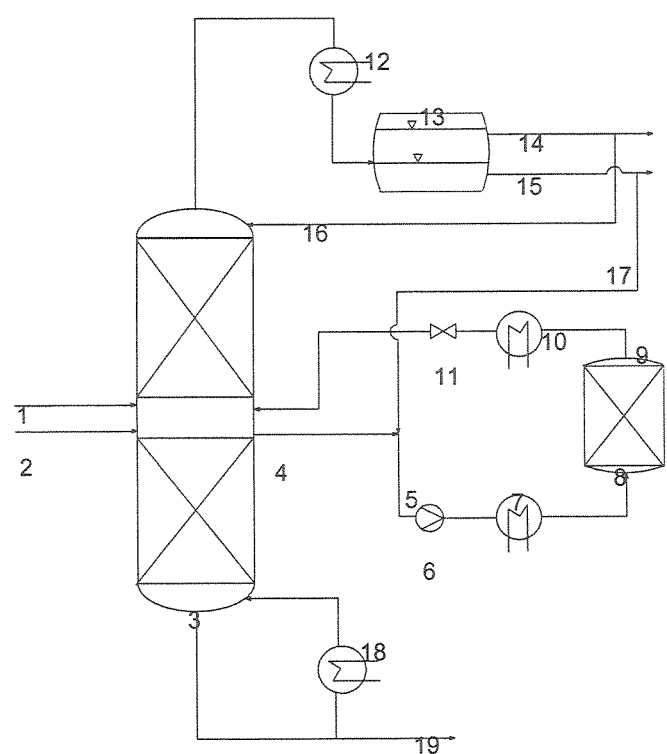

TRANSESTERIFICATION METHODS

CROSS-REFERENCE TO RELATED APPLICATIONS

The present application is a 35 U.S.C. §371 National Stage patent application of International patent application PCT/EP06/062283, filed on May 12, 2006, which claims priority to German patent application DE 102005023976.5, filed on May 20, 2005.

The present invention relates to processes for transesterifying organic acids with organic esters. Esters are generally prepared by reacting acids with alcohols or esters with an alcohol different from the alcohol radical of the ester. In specific cases, esters are, however, also obtained by transferring an alcohol radical from an organic ester to the acid group of an organic acid. This reaction is described, for example, in "Organikum", Wiley-VCH, 21st edition on page 494.

This reaction is in many cases advantageous if the direct reaction of the acid with the alcohol is difficult. Moreover, this type of reaction is preferred if the organic ester which is used as a reactant can be obtained inexpensively in large amounts or is obtained as a by-product.

However, the reaction detailed above has certain disadvantages. In particular, these arise as a result of the fact that the transesterification detailed above is generally an equilibrium reaction. Accordingly, a large amount of reactants originally used is included in the isolation of the products.

Moreover, the reaction described in the literature, owing to the problem detailed above, requires a relatively large amount of energy.

For these reasons, such a reaction has to date not been carried out on a larger scale.

In view of the prior art detailed above, it is thus an object of the invention to provide a process for transesterification which can be carried out simply and inexpensively.

It is a further object of the invention to provide a process in which the products can be obtained very selectively.

A further aim of the present invention is that of specifying a process for transesterification which can be carried out in high yields and with low energy consumption.

Moreover, the process of the present invention should be performable on the industrial scale.

These objects and further objects which are not stated explicitly but which can be derived or discerned directly from the connections discussed by way of introduction herein are achieved by processes having all features of claim 1. Appropriate modifications of the processes according to the invention are protected in the claims dependent upon claim 1.

By virtue of the transfer of the alcohol radical being performed in a still, it is possible in a not immediately foreseeable manner to provide a process comprising the steps of
A) mixing an organic acid a) with an ester b) and
B) transferring the alcohol radical of the ester b) to the acid a) to obtain the ester of the acid a) and the acid of the ester b),
which has a particularly low energy demand.

The process according to the invention additionally achieves the following advantages.

The products are obtained selectively and in many cases without formation of significant amounts of by-products.

The process according to the invention affords the product in high yields.

The process according to the invention can be carried out inexpensively, the energy demand being particularly low.

The process of the present invention can be carried out on the industrial scale.

According to the invention, an organic acid a) is mixed with an organic ester b). The term organic acid is common knowledge in the technical field. Typically, this is understood to mean compounds having groups of the formula —COOH, The organic acids may comprise one, two, three, four or more groups of the formula —COOH. These include in particular compounds of the formula R(—COOH)$_n$ in which the R radical is a group having from 1 to 30 carbon atoms, which comprises in particular 1-20, preferably 1-10, in particular 1-5 and more preferably 2-3 carbon atoms, and n is an integer in the range from 1 to 10, preferably 1 to 4 and more preferably 1 or 2.

The expression "group having 1 to 30 carbon atoms" designates radicals of organic compounds having 1 to 30 carbon atoms. In addition to aromatic and heteroaromatic groups, it also encompasses aliphatic and heteroaliphatic groups, for example alkyl, cycloalkyl, alkoxy, cycloalkoxy, cycloalkylthio and alkenyl groups. The groups mentioned may be branched or unbranched.

According to the invention, aromatic groups denote radicals of mono- or polycyclic aromatic compounds having preferably 6 to 20, in particular 6 to 12 carbon atoms.

Heteroaromatic groups denote aryl radicals in which at least one CH group has been replaced by N and/or at least two adjacent CH groups have been replaced by S, NH or O.

Aromatic or heteroaromatic groups preferred in accordance with the invention derive from benzene, naphthalene, biphenyl, diphenyl ether, diphenylmethane, diphenyldimethylmethane, bisphenone, diphenylsulphone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzooxathiadiazole, benzooxadiazole, benzopyridine, benzopyrazine, benzopyrazidine, benzopyrimidine, benzotriazine, indolizine, pyridopyridine, imidazopyrimidine, pyrazinopyrimidine, carbazole, aciridine, phenazine, benzoquinoline, phenoxazine, phenothiazine, acridizine, benzopteridine, phenanthroline and phenanthrene, each of which may also be substituted.

The preferred alkyl groups include the methyl, ethyl, propyl, isopropyl, 1-butyl, 2-butyl, 2-methylpropyl, tert-butyl radical, pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and the eicosyl group.

The preferred cycloalkyl groups include the cyclopropyl, cyclobutyl, cyclopentyl, cyclohexyl, cycloheptyl and the cyclooctyl group, each of which is optionally substituted with branched or unbranched alkyl groups.

The preferred alkenyl groups include the vinyl, allyl, 2-methyl-2-propenyl, 2-butenyl, 2-pentenyl, 2-decenyl and the 2-eicosenyl group.

The preferred heteroaliphatic groups include the aforementioned preferred alkyl and cycloalkyl radicals in which at least one carbon unit has been replaced by O, S or an $NR^8$ or $NR^8R^9$ group, and $R^8$ and $R^9$ are each independently an alkyl group having 1 to 6 carbon atoms, an alkoxy group having 1 to 6 carbon atoms or an aryl group.

Very particularly preferably in accordance with the invention, the inventive acids and/or esters have branched or unbranched alkyl or alkoxy groups having 1 to 20 carbon atoms, preferably 1 to 12, appropriately 1 to 6, in particular 1 to 4 carbon atoms, and cycloalkyl or cycloalkyloxy groups having 3 to 20 carbon atoms, preferably 5 to 6 carbon atoms.

The R radical may have substituents. The preferred substituents include halogens, in particular fluorine, chlorine, bromine, and also alkoxy or hydroxyl radicals.

The particularly preferred acids a) include (meth)acrylic acids. The term (meth)acrylic acids is known in the technical field, and is understood to mean not only acrylic acid and methacrylic acid but also derivatives of these acids. These derivatives include β-methylacrylic acid (butenoic acid), α,β-dimethylacrylic acid, β-ethylacrylic acid, and β,β-dimethylacrylic acid. Preference is given to acrylic acid (propenoic acid) and methacrylic acid (2-methylpropenoic acid).

The organic acids a) may be used individually or as a mixture of two, three or more different acids.

The organic ester b) used for the transesterification is likewise known in the technical field. Such compounds typically comprise groups of the formula —COO—R', in which R' is a group having 1 to 30 carbon atoms.

The organic esters may comprise one, two, three, four or more groups of the formula —COO—R'. These include in particular compounds of the formula $R(-COOR')_n$, in which the R radical is a group having 1 to 30 carbon atoms, which comprises in particular 1-20, preferably 1-10, in particular 1-5 and more preferably 2-3 carbon atoms, and n is an integer in the range from 1 to 10, preferably 1 to 4 and more preferably 1 or 2, and the R' radical is a group having 1 to 30 carbon atoms.

The term "group having 1 to 30 carbon atoms" has been defined above.

The acid radical of the ester b) differs from the organic acid a) in at least one feature. For example, the acid radical of the ester b) may have more carbon atoms than the organic acid a). Moreover, the ester b) may have a different substitution pattern from the acid a). For example, the acid radical of the ester b) may have different substituents, for example a different number of hydroxyl groups, from the acid a).

The boiling point of the organic ester b) is preferably less than the boiling point of the ester a) obtained from the acid a) by reaction. The difference in the boiling point is preferably at least 5° C., more preferably at least 10° C., this difference being based on a pressure of 1 bar and the boiling point of the pure substances.

The alcohol radical of the organic ester b) is likewise known in the technical field. The alcohol radical preferably has 1-20 carbon atoms, more preferably 1-10, in particular 1-5 and most preferably 1-3 carbon atoms. The alcohol radical may be derived from a saturated or unsaturated alcohol, and from an aromatic alcohol, for example phenol. The saturated alcohols used with preference include methanol, ethanol, propanol, butanol, in particular n-butanol and 2-methyl-1-propanol, pentanol, hexanol and 2-ethylhexanol.

The organic ester b) used is more preferably an alkyl α-hydroxycarboxylate. These include methyl α-hydroxypropionate, ethyl α-hydroxypropionate, methyl α-hydroxyisobutyrate and ethyl α-hydroxyisobutyrate.

The organic esters b) may be used individually or as a mixture of two, three or more different esters.

In step A), at least one organic acid a) is mixed with at least one organic ester b), for which any process known for this purpose can be used. This mixture can be prepared in a still. In addition, a mixture can also be prepared outside the still.

In step B), the alcohol radical of the organic ester b) is transferred to the organic acid a) to obtain the ester of the acid a) and the acid of the ester b). The conditions of this reaction also known as a transesterification are known per se.

The reaction is carried out preferably at temperatures in the range from 50° C. to 200° C., more preferably 70° C. to 130° C., in particular 80° C. to 120° C. and most preferably 90° C. to 110° C.

The reaction may be carried out at reduced or elevated pressure depending on the reaction temperature. This reaction is carried out preferably in the pressure range of 0.02-5 bar, in particular 0.2 to 3 bar and more preferably 0.3 to 0.5 bar.

The molar ratio of organic acid a) to the organic ester b) is preferably in the range of 4:1-1:4, in particular 3:1 to 1:3 and more preferably in the range of 2:1-1:2.

The transesterification can be carried out batchwise or continuously, preference being given to continuous processes.

The reaction time of the transesterification depends upon the molar masses used and the reaction temperature, these parameters lying within wide ranges. The reaction time of the transesterification of at least one organic ester b) with at least one organic acid a) is preferably in the range from 30 seconds to 15 hours, more preferably 5 minutes to 5 hours and most preferably 15 minutes to 3 hours.

In continuous processes, the residence time is preferably 30 seconds to 15 hours, more preferably 5 minutes to 5 hours and most preferably 15 minutes to 3 hours.

In the case of preparation of methyl methacrylate from methyl α-hydroxyisobutyrate, the temperature is preferably 60 to 130° C., more preferably 80 to 120° C. and most preferably 90 to 110° C. The pressure is preferably in the range from 50 to 1000 mbar, more preferably 300 to 800 mbar. The molar ratio of methacrylic acid to methyl α-hydroxyisobutyrate is preferably in the range of 2:1-1:2, in particular 1.5:1-1:1.5.

The selectivity is preferably at least 90%, more preferably 98%. The selectivity is defined as the ratio of the sum of amounts of organic esters a) and organic acids b) formed based on the sum of the amounts of organic esters b) and organic acids a) converted.

In addition to the reactants, the reaction mixture may comprise further constituents, for example solvents, catalysts, polymerization inhibitors and water.

The reaction of the organic ester b) with at least one organic acid a) can be catalysed by at least one acid or at least one base. It is possible to use either homogeneous or heterogeneous catalysts. Particularly suitable acidic catalysts are in particular inorganic acids, for example sulphuric acid or hydrochloric acid, and also organic acids, for example sulphonic acids, in particular p-toluenesulphonic acid, and acidic cation exchangers.

The particularly suitable cation exchange resins include in particular sulphonic acid-containing styrene-divinylbenzene polymers. Particularly suitable cation exchange resins may be obtained commercially from Rohm & Haas under the trade name Amberlyst® and from Bayer under the trade name Lewatit®.

The concentration of catalyst is preferably in the range from 1 to 30% by weight, more preferably 5 to 15% by weight, based on the sum of the organic ester b) used and of the organic acid a).

The polymerization inhibitors useable with preference include phenothiazine, tert-butylcatechol, hydroquinone monomethyl ether, hydroquinone, 4-hydroxy-2,2,6,6-tetramethylpiperidinooxyl (TEMPOL) or mixtures thereof; the effectiveness of these inhibitors being improvable in some cases by use of oxygen. The polymerization inhibitors may be used in a concentration in the range from 0.001 to 2.0% by weight, more preferably in the range from 0.01 to 0.2% by weight, based on the sum of the organic ester b) used and of the organic acid a).

In a particular aspect of the present invention, the transesterification can be effected in the presence of water. The water content is preferably in the range of 0.1-50% by weight, more preferably 0.5-20% by weight and most preferably 1-10% by weight, based on the weight of the organic ester b) used.

The addition of small amounts of water can surprisingly increase the selectivity of the reaction. In spite of addition of water, the formation of methanol can at the same time be kept surprisingly low. At a water concentration of 10 to 15% by weight, based on the weight of the organic ester b) used, preferably less than 5% by weight of methanol is formed at a reaction temperature of 120° C. and a reaction time or residence time of 5 to 180 min.

According to the invention, the transfer of the alcohol radical of the organic ester b) to the organic acid a), i.e. the transesterification, is effected in a still. Distillation units suitable for this purpose are common knowledge and are in many cases used for separation.

At least one organic ester b), for example an alkyl α-hydroxycarboxylate, and at least one organic acid a), for example (meth)acrylic acid, may be introduced individually or as a mixture into the still. The distillation conditions are preferably selected such that exactly one product is passed out of the still by distillation, the second product remaining in the bottom and being removed therefrom continuously. The ester a) obtained by the reaction is preferably removed by distillation, while the resulting acid b) is passed out of the bottom.

The still may be produced from any material suitable therefor. These include stainless steel and inert materials.

If a catalyst is used, it may be provided in each region of the still. For example, the catalyst may be provided in the region of the bottom or in the region of the column. In this case, the reactants should, however, be brought into contact with the catalyst.

In addition, catalysts may be provided in a separate region of the still, in which case this region is connected to the further regions of the still, for example the bottom and/or the column. This separate arrangement of the catalyst region is preferred, in which case the reactants can be passed cyclically through the catalyst region. This continuously forms the ester of organic acid a), for example alkyl (meth)acrylate, and also the acid of the organic ester b), for example α-hydroxycarboxylic acid.

By virtue of this preferred embodiment, it is surprisingly possible to increase the selectivity of the reaction. In this context, it should be emphasized that the pressure of the reaction can be adjusted independently of the pressure within the distillation columns. This allows the boiling temperature to be kept low without the reaction time or the residence time rising correspondingly. In addition, the temperature of the reaction can be varied over a wide range. This allows the reaction time to be shortened. In addition, the volume of catalyst can be selected as desired without having to take account of the geometry of the column. Moreover, it is possible, for example, to add a further reactant. All of these measures can contribute to an increase in the selectivity and the productivity, surprising synergistic effects being achieved.

A preferred embodiment of a still is shown schematically in FIG. 1. The reactants may be introduced into the distillation column (3) via one common line (1) or separately via two lines (1) and (2). The reactants are preferably added via separate lines. The reactants can be fed at the same stage or in any position in the column.

The temperature of the reactants can be adjusted by means of a heat exchanger in the feed, the units needed for this purpose not being shown in FIG. 1. In a preferred variant, the reactants are metered separately into the column, the lower-boiling components being metered in below the position for the feeding of the higher-boiling compounds. In this case, the lower-boiling component is preferably added in vaporous form.

For the present invention, any multistage distillation column (3) may be used which has two or more separating stages. The number of separating stages used in the present invention is the number of trays in a tray column or the number of vertical plates in the case of a column with structured packing or a column with random packings.

Examples of a multistage distillation column with trays include those having bubble-cap trays, sieve trays, tunnel-cap trays, valve trays, slot trays, slotted sieve trays, bubble-cap sieve trays, jet trays, centrifugal trays; for a multistage distillation column with random packings, those such as Raschig rings, Lessing rings, Pall rings, Berl saddles, Intalox saddles; and, for a multistage distillation column with structured packings, those such as Mellapak (Sulzer), Rombopak (Kuhni), Montz-Pak (Montz) and structured packings with catalyst pockets, for example Kata-Pak.

A distillation column with combinations of regions of trays, of regions of random packings or of regions of structured packings may likewise be used.

The column (3) may be equipped with internals. The column preferably has a condenser (12) for condensing the vapour and a bottom evaporator (18).

The distillation apparatus preferably has at least one region, known hereinafter as reactor, in which at least one catalyst is provided. This reactor may be within the distillation column. However, this reactor is preferably arranged outside the column (3) in a separate region, one of these preferred embodiments being explained in detail in FIG. 1.

In order to carry out the transesterification reaction in a separate reactor (8), it is possible within the column to collect a portion of the liquid phase flowing downwards by means of a collector and to pass it out of the column as a substream (4). The position of the collector is determined by the concentration profile in the column of the individual components. The concentration profile can be regulated by means of the temperature and/or the reflux. The collector is preferably positioned such that the stream conducted out of the column contains both reactants, more preferably the reactants in sufficiently high concentration and most preferably in a molar acid:ester ratio=1.5:1 to 1:1.5. In addition, a plurality of collectors may be provided at various points in the distillation column, in which case the amount of reactants withdrawn can be used to adjust the molar ratios.

It is additionally possible for a further reactant, for example water, to be metered into the stream conducted out of the column, in order to adjust the acid/ester product ratio in the cross-transesterification reaction or to increase the selectivity. The water can be fed from outside via a line (not shown in FIG. 1) or from a phase separator (13). The pressure of the stream (5) enriched with water can then be increased by a means for pressure increase (6), for example a pump.

An increase in the pressure can reduce or prevent formation of steam in the reactor, for example a fixed bed reactor. This allows uniform flow-through of the reactor and wetting of the catalyst particles. The stream can be conducted through a heat exchanger (7) and the reaction temperature adjusted. The stream can be heated or cooled as required. It is additionally possible to adjust the ester to acid product ratio via the reaction temperature.

The transesterification reaction takes place over the catalyst in the fixed bed reactor (8). The flow through the reactor may be downwards or upwards. The reactor output stream (9) comprising the products and the unconverted reactants to a certain degree, the content of the components in the reactor waste stream depending upon the residence time, the catalyst mass, the reaction temperature and the reactant ratio and the amount of water added, is first passed through a heat exchanger (10) and adjusted to a temperature which is advantageous for the introduction into the distillation column. Preference is given to setting the temperature which corresponds to the temperature in the distillation column at the point of introduction of the stream.

The position where the stream leaving the reactor is returned into the column may lie above or below the position for the withdrawal of the reactor feed, but will preferably be above it. Before the recycling into the column, the stream may be decompressed through a valve (11), which preferably establishes the same pressure level as in the column. In this context, the distillation column preferably has a lower pressure. This configuration offers the advantage that the boiling points of the components to be separated are lower, as a result of which the distillation can be carried out at a lower temperature level, as a result of which it saves energy and is more thermally gentle.

In the distillation column (3), the product mixture is then separated. The low boiler, preferably the ester formed in the transesterification, is removed via the top. The distillation column is preferably operated such that the water added upstream of the fixed bed reactor is likewise removed as the top product. The vaporous stream drawn off at the top is condensed in a condenser (12) and then separated in a decanter (13) into the aqueous phase and product ester-containing phase. The aqueous phase can be discharged to the workup via a line (15) or returned fully or partly back into the reaction via line (17). The stream of the ester-containing phase can be conducted via line (14) partly as reflux (16) to the column or discharged partly from the still. The high boiler, preferably the acid formed in the cross-transesterification, is discharged from the column (19) as a bottom stream.

The present invention will be illustrated in detail hereinafter with reference to examples and to a comparative example.

EXAMPLE 1

In a reactive still shown in FIG. 1, 4619 g of methyl α-hydroxyisobutyrate (MHIB) and 3516 g of methacrylic acid (MA) were fed in over a period of 48 hours. The reaction was carried out at a temperature of 120° C. and a pressure of 250 mbar. α-Hydroxyisobutyric acid (HIBA) formed was removed from the bottom. Methyl methacrylate (MMA) was distilled off. The reaction was carried out in the presence of 16% by weight of water based on the weight of methyl α-hydroxyisobutyrate. The reaction was carried out using an acidic catalyst (cation exchanger; Lewatit® K2431 from Bayer).

This gives rise to a selectivity of 99%, which is defined as the ratio of the sum of amounts of MMA and HIBA formed to the sum of the amounts of MHIB and MA converted.

EXAMPLES 2 TO 18

Example 1 was essentially repeated, except that no water was added to the reaction mixture. The reaction was effected under the conditions specified in Table 1, especially with regard to temperature, residence time and molar ratio of the reactants. The selectivity, defined as the ratio of amounts of MMA and HIBA formed to amounts of MHIB and MA converted, of the reactions is likewise shown in Table 1.

TABLE 1

| Example | Reaction temperature [° C.] | Molar MHIB/MA ratio | Residence time [min] | Selectivity [%] |
|---------|------|------|--------|-------|
| 2  | 120 | 1.00 | 28.33  | 93.21 |
| 3  | 90  | 1.00 | 42.50  | 95.06 |
| 4  | 100 | 1.00 | 42.50  | 94.81 |
| 5  | 110 | 1.00 | 42.50  | 94.64 |
| 6  | 120 | 1.00 | 42.50  | 90.67 |
| 7  | 90  | 1.00 | 85.00  | 95.53 |
| 8  | 100 | 1.00 | 85.00  | 94.95 |
| 9  | 110 | 1.00 | 85.00  | 93.55 |
| 10 | 120 | 1.00 | 85.00  | 91.78 |
| 11 | 90  | 1.00 | 170.00 | 94.83 |
| 12 | 100 | 1.00 | 170.00 | 94.06 |
| 13 | 90  | 2.0  | 42.50  | 91.61 |
| 14 | 100 | 2.0  | 42.50  | 91.73 |
| 15 | 90  | 2.0  | 85.00  | 90.63 |
| 16 | 100 | 2.0  | 85.00  | 90.30 |
| 17 | 120 | 0.50 | 28.33  | 92.05 |
| 18 | 120 | 0.50 | 42.50  | 92.62 |

EXAMPLES 19 TO 38

Example 1 was essentially repeated, except that the reaction was carried out under the conditions specified in Table 2, especially with regard to the temperature and residence time. The molar ratio of MHIB/MA was 1:1. In addition, different proportions of water were added, which are likewise listed in Table 2. The selectivity, defined as the ratio of amounts of MMA and HIBA formed to amounts of MHIB and MA converted, of the reactions and the molar ratio of HIBA to MMA are likewise listed in Table 2.

TABLE 2

| Ex. | Reaction temperature [° C.] | Molar H$_2$O to MHIB ratio | Residence time [min] | Selectivity [%] | Molar HIBA to MMA ratio |
|-----|------|------|------|-------|------|
| 19 | 90  | 0.20 | 42.5 | 98.61 | 1.33 |
| 20 | 100 | 0.20 | 42.5 | 98.18 | 1.21 |
| 21 | 110 | 0.20 | 42.5 | 97.44 | 1.11 |
| 22 | 120 | 0.20 | 42.5 | 96.27 | 0.99 |
| 23 | 90  | 0.20 | 85   | 98.34 | 1.18 |
| 24 | 100 | 0.20 | 85   | 97.66 | 1.09 |
| 25 | 110 | 0.20 | 85   | 96.56 | 1.02 |
| 26 | 100 | 0.20 | 170  | 96.95 | 1.00 |
| 27 | 90  | 0.50 | 42.5 | 98.80 | 1.61 |
| 28 | 100 | 0.50 | 42.5 | 98.64 | 1.36 |
| 29 | 110 | 0.50 | 42.5 | 98.21 | 1.22 |
| 30 | 120 | 0.50 | 42.5 | 97.58 | 1.08 |
| 31 | 90  | 0.50 | 85   | 98.76 | 1.39 |
| 32 | 100 | 0.50 | 85   | 98.35 | 1.20 |
| 33 | 110 | 0.50 | 85   | 97.78 | 1.10 |
| 34 | 100 | 0.50 | 170  | 98.08 | 1.10 |

TABLE 2-continued

| Ex. | Reaction temperature [° C.] | Molar H$_2$O to MHIB ratio | Residence time [min] | Selectivity [%] | Molar HIBA to MMA ratio |
|---|---|---|---|---|---|
| 35 | 90 | 1.00 | 50.0 | 99.41 | 2.090 |
| 36 | 100 | 1.00 | 50.0 | 99.65 | 1.618 |
| 37 | 110 | 1.00 | 50.0 | 99.82 | 1.360 |
| 38 | 120 | 1.00 | 50.0 | 99.54 | 1.319 |

The above examples show that the present invention can form esters with high selectivity, the ratio of the products, for example of alkyl (meth)acrylate to α-hydroxycarboxylic acid, being close to 1 even at relatively high water concentrations.

Accordingly, relatively little methanol is formed. The molar ratio of the products can also be controlled via the temperature.

The invention claimed is:

1. A process for transesterification comprising:
   A) mixing methacrylic acid with at least one ester; and
   B) transferring an alcohol radical of the at least one ester to the methacrylic acid to obtain an ester of methacrylic acid and an acid of the at least one ester;
   wherein:
   B) is carried out in an apparatus comprising at least one distillation column and at least one reactor;
   the at least one ester comprises an alkyl α-hydroxycarboxylate;
   the reaction mixture comprises at least one polymerization inhibitor selected from the group consisting of phenothiazine, tert-butylcatechol, hydroquinone monomethyl ether, hydroquinone, and 4-hydroxy-2,2,6,6-tetramethylpiperidinooxyl; and
   the apparatus further comprises at least one line between at least one distillation column and at least one reactor equipped with a means for increasing pressure.

2. The process according to claim 1, wherein the process is carried out continuously.

3. The process according to claim 1, wherein B) is carried out under acid catalysis.

4. The process according to claim 1, wherein an alcohol radical of the at least one ester comprises from 1 to 10 carbon atoms.

5. The process according to claim 4, wherein the at least one ester comprises a 2-hydroxypropanoic ester and/or a 2-hydroxybutanoic ester.

6. The process according to claim 1, wherein an alcohol radical of the at least one ester is derived from methanol and/or ethanol.

7. The process according to claim 1, wherein the transesterification is carried out at a temperature in the range from 50° C. to 200° C.

8. The process according to claim 1, wherein the transesterification is carried out in the presence of water.

9. The process according to claim 8, wherein the water concentration is 0.1 to 50% by weight based on the weight of the at least one ester.

10. The process according to claim 1, wherein the at least one ester comprises methyl α-hydroxyisobutyrate.

11. The process according to claim 1, wherein the at least one ester is selected from the group consisting of methyl α-hydroxypropionate, methyl α-hydroxyisobutyrate and ethyl α-hydroxyisobutyrate.

12. The process according to claim 1, wherein the means for increasing pressure is a pump.

* * * * *